United States Patent
Bardy et al.

(10) Patent No.: US 9,504,423 B1
(45) Date of Patent: Nov. 29, 2016

(54) METHOD FOR ADDRESSING MEDICAL CONDITIONS THROUGH A WEARABLE HEALTH MONITOR WITH THE AID OF A DIGITAL COMPUTER

(71) Applicant: Bardy Diagnostics, Inc., Vashon, WA (US)

(72) Inventors: Gust H. Bardy, Carnation, WA (US); Jon Mikalson Bishay, Seattle, WA (US)

(73) Assignee: BARDY DIAGNOSTICS, INC., Vashon, WA (US)

( * ) Notice: Subject to any disclaimer, the term of this patent is extended or adjusted under 35 U.S.C. 154(b) by 0 days.

(21) Appl. No.: 14/875,622

(22) Filed: Oct. 5, 2015

(51) Int. Cl.
| | |
|---|---|
| *A61B 5/0408* | (2006.01) |
| *A61B 5/00* | (2006.01) |
| *A61B 5/0402* | (2006.01) |
| *A61B 5/046* | (2006.01) |
| *A61B 5/0468* | (2006.01) |
| *A61B 5/0464* | (2006.01) |

(Continued)

(52) U.S. Cl.
CPC .......... *A61B 5/6823* (2013.01); *A61B 5/0006* (2013.01); *A61B 5/0022* (2013.01); *A61B 5/01* (2013.01); *A61B 5/021* (2013.01); *A61B 5/0245* (2013.01); *A61B 5/0402* (2013.01); *A61B 5/046* (2013.01); *A61B 5/0464* (2013.01); *A61B 5/0468* (2013.01); *A61B 5/0816* (2013.01); *A61B 5/1477* (2013.01); *A61B 5/14532* (2013.01); *A61B 5/14542* (2013.01); *A61B 5/7246* (2013.01); *A61B 5/7282* (2013.01); *A61B 5/746* (2013.01); *A61B 2560/0214* (2013.01); *A61B 2560/0475* (2013.01); *A61B 2562/04* (2013.01)

(58) Field of Classification Search
None
See application file for complete search history.

(56) References Cited

U.S. PATENT DOCUMENTS

| | | |
|---|---|---|
| 3,215,136 A | 11/1965 | Holter et al. |
| 3,699,948 A | 10/1972 | Ota et al. |

(Continued)

FOREIGN PATENT DOCUMENTS

| | | |
|---|---|---|
| DE | 19955211 | 5/2001 |
| EP | 1859833 | 11/2007 |

(Continued)

OTHER PUBLICATIONS

US 6,527,714, 03/2003, Bardy (withdrawn)

(Continued)

*Primary Examiner* — Neal Sereboff
(74) *Attorney, Agent, or Firm* — Patrick J. S. Inouye

(57) ABSTRACT

Individuals who suffer from certain kinds of medical conditions, particularly conditions that only sporadically exhibit measurable symptoms, can feel helpless in their attempts to secure access to medical care because, at least in part, they are left to the mercy of their condition to present symptoms at the right time to allow diagnosis and treatment. Providing these individuals with ambulatory extended-wear health monitors that record ECG and physiology, preferably available over-the-counter and without health insurance preauthorization, is a first step towards addressing their needs. In addition, these individuals need a way to gain entry into the health care system once a medically-actionable medical condition has been identified. Here, the ECG and physiology is downloaded and evaluated post-monitoring against medical diagnostic criteria. Medical specialists are pre-identified and paired up with key diagnostic findings, such that an individual whose monitoring data indicates a medical concern will be automatically referred and treated.

10 Claims, 5 Drawing Sheets

(51) Int. Cl.
  *A61B 5/0245* (2006.01)
  *A61B 5/021* (2006.01)
  *A61B 5/08* (2006.01)
  *A61B 5/01* (2006.01)
  *A61B 5/145* (2006.01)
  *A61B 5/1477* (2006.01)

(56) References Cited

U.S. PATENT DOCUMENTS

| | | |
|---|---|---|
| 3,893,453 A | 7/1975 | Goldberg |
| 4,123,785 A | 10/1978 | Cherry et al. |
| 4,328,814 A | 5/1982 | Arkans |
| 4,532,934 A | 8/1985 | Kelen |
| 4,550,502 A | 11/1985 | Grayzel |
| 4,716,903 A | 1/1988 | Hansen |
| 4,809,705 A | 3/1989 | Ascher |
| 4,915,656 A | 4/1990 | Alferness |
| 5,025,794 A | 6/1991 | Albert et al. |
| 5,168,876 A | 12/1992 | Quedens et al. |
| 5,215,098 A | 6/1993 | Steinhaus |
| D341,423 S | 11/1993 | Bible |
| 5,341,806 A | 8/1994 | Gadsby et al. |
| 5,355,891 A | 10/1994 | Wateridge et al. |
| 5,365,934 A | 11/1994 | Leon et al. |
| 5,392,784 A | 2/1995 | Gudaitis |
| D357,069 S | 4/1995 | Plahn et al. |
| 5,402,780 A | 4/1995 | Faasse, Jr. |
| 5,402,884 A | 4/1995 | Gilman et al. |
| 5,458,141 A | 10/1995 | Neil |
| 5,473,537 A | 12/1995 | Glazer et al. |
| 5,483,969 A | 1/1996 | Testerman et al. |
| 5,511,553 A | 4/1996 | Segalowitz |
| 5,540,733 A | 7/1996 | Testerman et al. |
| 5,546,952 A | 8/1996 | Erickson |
| 5,549,655 A | 8/1996 | Erickson |
| 5,579,919 A | 12/1996 | Gilman et al. |
| 5,582,181 A | 12/1996 | Ruess |
| D377,983 S | 2/1997 | Sabri et al. |
| 5,601,089 A | 2/1997 | Bledsoe et al. |
| 5,623,935 A | 4/1997 | Faisandier |
| 5,682,901 A | 11/1997 | Kamen |
| 5,697,955 A | 12/1997 | Stolte |
| 5,749,902 A | 5/1998 | Olsen et al. |
| 5,817,151 A | 10/1998 | Olsen et al. |
| 5,819,741 A | 10/1998 | Karlsson et al. |
| 5,850,920 A | 12/1998 | Gilman et al. |
| D407,159 S | 3/1999 | Roberg |
| 5,906,583 A | 5/1999 | Rogel |
| 5,951,598 A | 9/1999 | Bishay et al. |
| 5,957,857 A | 9/1999 | Hartley |
| 5,984,102 A | 11/1999 | Tay |
| 6,032,064 A | 2/2000 | Devlin et al. |
| 6,038,469 A | 3/2000 | Karlsson et al. |
| 6,101,413 A | 8/2000 | Olsen et al. |
| 6,115,638 A | 9/2000 | Groenke |
| 6,117,077 A | 9/2000 | Del Mar et al. |
| 6,134,479 A | 10/2000 | Brewer et al. |
| 6,148,233 A | 11/2000 | Owen et al. |
| 6,149,602 A | 11/2000 | Arcelus |
| 6,149,781 A * | 11/2000 | Forand ............... C25F 1/00 204/239 |
| 6,188,407 B1 | 2/2001 | Smith et al. |
| D443,063 S | 5/2001 | Pisani et al. |
| 6,245,025 B1 | 6/2001 | Torok et al. |
| 6,246,330 B1 * | 6/2001 | Nielsen ............... A61F 13/42 340/384.1 |
| D445,507 S | 7/2001 | Pisani et al. |
| 6,269,267 B1 | 7/2001 | Bardy et al. |
| 6,272,385 B1 | 8/2001 | Bishay et al. |
| 6,298,255 B1 | 10/2001 | Cordero et al. |
| 6,301,502 B1 | 10/2001 | Owen et al. |
| 6,304,773 B1 | 10/2001 | Taylor et al. |
| 6,304,780 B1 | 10/2001 | Owen et al. |
| 6,304,783 B1 | 10/2001 | Lyster et al. |
| 6,374,138 B1 | 4/2002 | Owen et al. |
| 6,418,342 B1 | 7/2002 | Owen et al. |
| 6,424,860 B1 | 7/2002 | Karlsson et al. |
| 6,427,083 B1 | 7/2002 | Owen et al. |
| 6,456,872 B1 | 9/2002 | Faisandier |
| 6,546,285 B1 | 4/2003 | Owen et al. |
| 6,605,046 B1 | 8/2003 | Del Mar |
| 6,607,485 B2 | 8/2003 | Bardy |
| 6,611,705 B2 | 8/2003 | Hopman et al. |
| 6,671,545 B2 | 12/2003 | Fincke |
| 6,671,547 B2 | 12/2003 | Lyster et al. |
| 6,694,186 B2 | 2/2004 | Bardy |
| 6,704,595 B2 | 3/2004 | Bardy |
| 6,705,991 B2 | 3/2004 | Bardy |
| 6,719,701 B2 | 4/2004 | Lade |
| 6,754,523 B2 | 6/2004 | Toole |
| 6,782,293 B2 | 8/2004 | Dupelle et al. |
| 6,856,832 B1 | 2/2005 | Matsumura et al. |
| 6,860,897 B2 | 3/2005 | Bardy |
| 6,866,629 B2 | 3/2005 | Bardy |
| 6,887,201 B2 | 5/2005 | Bardy |
| 6,893,397 B2 | 5/2005 | Bardy |
| 6,904,312 B2 | 6/2005 | Bardy |
| 6,908,431 B2 | 6/2005 | Bardy |
| 6,913,577 B2 | 7/2005 | Bardy |
| 6,944,498 B2 | 9/2005 | Owen et al. |
| 6,960,167 B2 | 11/2005 | Bardy |
| 6,978,169 B1 | 12/2005 | Guerra |
| 6,993,377 B2 | 1/2006 | Flick et al. |
| 7,020,508 B2 | 3/2006 | Stivoric et al. |
| 7,027,864 B2 | 4/2006 | Snyder et al. |
| 7,065,401 B2 | 6/2006 | Worden |
| 7,085,601 B1 | 8/2006 | Bardy et al. |
| 7,104,955 B2 | 9/2006 | Bardy |
| 7,134,996 B2 | 11/2006 | Bardy |
| 7,137,389 B2 | 11/2006 | Berthon-Jones |
| 7,147,600 B2 | 12/2006 | Bardy |
| 7,215,991 B2 | 5/2007 | Besson et al. |
| 7,248,916 B2 | 7/2007 | Bardy |
| 7,257,438 B2 | 8/2007 | Kinast |
| 7,277,752 B2 | 10/2007 | Matos |
| D558,882 S | 1/2008 | Brady et al. |
| 7,328,061 B2 | 2/2008 | Rowlandson |
| 7,412,395 B2 | 8/2008 | Rowlandson |
| 7,429,938 B1 | 9/2008 | Corndorf |
| D606,656 S | 12/2009 | Kobayashi et al. |
| 7,706,870 B2 | 4/2010 | Shieh et al. |
| 7,756,721 B1 | 7/2010 | Falchuk et al. |
| 7,787,943 B2 | 8/2010 | McDonough |
| 7,874,993 B2 | 1/2011 | Bardy |
| 7,881,785 B2 | 2/2011 | Nassif et al. |
| D639,437 S | 6/2011 | Bishay et al. |
| 7,959,574 B2 | 6/2011 | Bardy |
| 8,116,841 B2 | 2/2012 | Bly et al. |
| 8,172,761 B1 | 5/2012 | Rulkov et al. |
| 8,180,425 B2 | 5/2012 | Selvitelli et al. |
| 8,200,320 B2 | 6/2012 | Kovacs |
| 8,231,539 B2 | 7/2012 | Bardy |
| 8,231,540 B2 | 7/2012 | Bardy |
| 8,239,012 B2 | 8/2012 | Felix et al. |
| 8,249,686 B2 | 8/2012 | Libbus et al. |
| 8,260,414 B2 | 9/2012 | Nassif et al. |
| 8,266,008 B1 | 9/2012 | Siegal et al. |
| 8,277,378 B2 | 10/2012 | Bardy |
| 8,285,356 B2 | 10/2012 | Bly et al. |
| 8,285,370 B2 | 10/2012 | Felix et al. |
| 8,308,650 B2 | 11/2012 | Bardy |
| 8,366,629 B2 | 2/2013 | Bardy |
| 8,374,688 B2 | 2/2013 | Libbus et al. |
| 8,412,317 B2 | 4/2013 | Mazar |
| 8,460,189 B2 | 6/2013 | Libbus et al. |
| 8,473,047 B2 | 6/2013 | Chakravarthy et al. |
| 8,478,418 B2 | 7/2013 | Fahey |
| 8,554,311 B2 | 10/2013 | Warner et al. |
| 8,591,430 B2 | 11/2013 | Amurthur et al. |
| 8,594,763 B1 | 11/2013 | Bibian et al. |
| 8,613,708 B2 | 12/2013 | Bishay et al. |
| 8,613,709 B2 | 12/2013 | Bishay et al. |
| 8,620,418 B1 | 12/2013 | Kuppuraj et al. |
| 8,626,277 B2 | 1/2014 | Felix et al. |

(56) References Cited

U.S. PATENT DOCUMENTS

| | | |
|---|---|---|
| 8,668,653 B2 | 3/2014 | Nagata et al. |
| 8,684,925 B2 | 4/2014 | Manicka et al. |
| 8,688,190 B2 | 4/2014 | Libbus et al. |
| 8,718,752 B2 | 5/2014 | Libbus et al. |
| 8,744,561 B2 | 6/2014 | Fahey |
| 8,774,932 B2 | 7/2014 | Fahey |
| 8,790,257 B2 | 7/2014 | Libbus et al. |
| 8,790,259 B2 | 7/2014 | Katra et al. |
| 8,795,174 B2 | 8/2014 | Manicka et al. |
| 8,798,734 B2 | 8/2014 | Kuppuraj et al. |
| 8,818,478 B2 | 8/2014 | Scheffler et al. |
| 8,818,481 B2 | 8/2014 | Bly et al. |
| 8,823,490 B2 | 9/2014 | Libbus et al. |
| 9,277,864 B2 | 3/2016 | Yang et al. |
| 2002/0013538 A1 | 1/2002 | Teller |
| 2002/0013717 A1 | 1/2002 | Ando et al. |
| 2002/0103422 A1 | 8/2002 | Harder et al. |
| 2002/0120310 A1 | 8/2002 | Linden et al. |
| 2002/0184055 A1 | 12/2002 | Naghavi et al. |
| 2002/0193668 A1 | 12/2002 | Munneke |
| 2003/0004547 A1 | 1/2003 | Owen et al. |
| 2003/0073916 A1 | 4/2003 | Yonce |
| 2003/0083559 A1 | 5/2003 | Thompson |
| 2003/0097078 A1 | 5/2003 | Maeda |
| 2003/0139785 A1 | 7/2003 | Riff et al. |
| 2003/0176802 A1 | 9/2003 | Galen et al. |
| 2003/0211797 A1 | 11/2003 | Hill et al. |
| 2004/0008123 A1 | 1/2004 | Carrender |
| 2004/0019288 A1 | 1/2004 | Kinast |
| 2004/0034284 A1 | 2/2004 | Aversano et al. |
| 2004/0049132 A1 | 3/2004 | Barron et al. |
| 2004/0073127 A1 | 4/2004 | Istvan et al. |
| 2004/0087836 A1 | 5/2004 | Green et al. |
| 2004/0093192 A1 | 5/2004 | Hasson et al. |
| 2004/0148194 A1 | 7/2004 | Wellons et al. |
| 2004/0207530 A1 * | 10/2004 | Nielsen ............ A61F 13/42 340/604 |
| 2004/0236202 A1 | 11/2004 | Burton |
| 2004/0243435 A1 | 12/2004 | Williams |
| 2004/0256453 A1 | 12/2004 | Lammle |
| 2004/0260188 A1 | 12/2004 | Syed et al. |
| 2004/0260192 A1 | 12/2004 | Yamamoto |
| 2005/0096717 A1 | 5/2005 | Bishay et al. |
| 2005/0108055 A1 | 5/2005 | Ott et al. |
| 2005/0154267 A1 | 7/2005 | Bardy |
| 2005/0182308 A1 | 8/2005 | Bardy |
| 2005/0182309 A1 | 8/2005 | Bardy |
| 2005/0215918 A1 | 9/2005 | Frantz et al. |
| 2005/0222513 A1 | 10/2005 | Hadley et al. |
| 2005/0228243 A1 | 10/2005 | Bardy |
| 2005/0245839 A1 | 11/2005 | Stivoric et al. |
| 2006/0025696 A1 | 2/2006 | Kurzweil et al. |
| 2006/0025824 A1 | 2/2006 | Freeman et al. |
| 2006/0041201 A1 | 2/2006 | Behbehani et al. |
| 2006/0122469 A1 | 6/2006 | Martel |
| 2006/0224072 A1 | 10/2006 | Shennib |
| 2006/0235320 A1 | 10/2006 | Tan et al. |
| 2006/0253006 A1 | 11/2006 | Bardy |
| 2006/0264730 A1 | 11/2006 | Stivoric et al. |
| 2007/0003115 A1 | 1/2007 | Patton et al. |
| 2007/0050209 A1 | 3/2007 | Yered |
| 2007/0078324 A1 | 4/2007 | Wijisiriwardana |
| 2007/0093719 A1 | 4/2007 | Nichols, Jr. et al. |
| 2007/0100248 A1 | 5/2007 | Van Dam et al. |
| 2007/0100667 A1 | 5/2007 | Bardy |
| 2007/0123801 A1 | 5/2007 | Goldberger et al. |
| 2007/0136091 A1 | 6/2007 | McTaggart |
| 2007/0179357 A1 | 8/2007 | Bardy |
| 2007/0185390 A1 | 8/2007 | Perkins et al. |
| 2007/0203415 A1 | 8/2007 | Bardy |
| 2007/0203423 A1 | 8/2007 | Bardy |
| 2007/0208233 A1 | 9/2007 | Kovacs |
| 2007/0208266 A1 | 9/2007 | Hadley |
| 2007/0225611 A1 | 9/2007 | Kumar et al. |
| 2007/0244405 A1 | 10/2007 | Xue et al. |
| 2007/0249946 A1 | 10/2007 | Kumar et al. |
| 2007/0255153 A1 | 11/2007 | Kumar et al. |
| 2007/0265510 A1 | 11/2007 | Bardy |
| 2007/0276270 A1 | 11/2007 | Tran |
| 2007/0276275 A1 | 11/2007 | Proctor et al. |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293772 A1 | 12/2007 | Bardy |
| 2007/0299325 A1 | 12/2007 | Farrell et al. |
| 2007/0299617 A1 | 12/2007 | Willis |
| 2008/0051668 A1 | 2/2008 | Bardy |
| 2008/0058661 A1 | 3/2008 | Bardy |
| 2008/0091097 A1 | 4/2008 | Linti et al. |
| 2008/0139953 A1 | 6/2008 | Baker et al. |
| 2008/0194927 A1 | 8/2008 | KenKnight et al. |
| 2008/0208009 A1 | 8/2008 | Shklarski |
| 2008/0208014 A1 | 8/2008 | KenKnight et al. |
| 2008/0284599 A1 | 11/2008 | Zdeblick et al. |
| 2008/0288026 A1 | 11/2008 | Cross et al. |
| 2008/0306359 A1 | 12/2008 | Zdeblick et al. |
| 2009/0054952 A1 | 2/2009 | Glukhovsky et al. |
| 2009/0069867 A1 | 3/2009 | KenKnight et al. |
| 2009/0073991 A1 | 3/2009 | Landrum et al. |
| 2009/0076336 A1 | 3/2009 | Mazar et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0112116 A1 | 4/2009 | Lee et al. |
| 2009/0131759 A1 | 5/2009 | Sims et al. |
| 2009/0216132 A1 | 8/2009 | Orbach |
| 2009/0270708 A1 | 10/2009 | Shen et al. |
| 2009/0270747 A1 | 10/2009 | Van Dam et al. |
| 2009/0292194 A1 | 11/2009 | Libbus et al. |
| 2010/0022897 A1 | 1/2010 | Parker et al. |
| 2010/0056881 A1 | 3/2010 | Libbus et al. |
| 2010/0081913 A1 | 4/2010 | Cross et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0234715 A1 | 9/2010 | Shin et al. |
| 2010/0234716 A1 | 9/2010 | Engel |
| 2010/0280366 A1 | 11/2010 | Arne et al. |
| 2010/0324384 A1 | 12/2010 | Moon et al. |
| 2011/0054286 A1 | 3/2011 | Crosby et al. |
| 2011/0066041 A1 | 3/2011 | Pandia et al. |
| 2011/0077497 A1 | 3/2011 | Oster et al. |
| 2011/0144470 A1 | 6/2011 | Mazar et al. |
| 2011/0160548 A1 | 6/2011 | Forster et al. |
| 2011/0224564 A1 | 9/2011 | Moon et al. |
| 2011/0237924 A1 | 9/2011 | McGusty et al. |
| 2011/0245699 A1 | 10/2011 | Snell et al. |
| 2011/0245711 A1 | 10/2011 | Katra et al. |
| 2012/0003933 A1 | 1/2012 | Baker et al. |
| 2012/0029306 A1 | 2/2012 | Paquet et al. |
| 2012/0029316 A1 | 2/2012 | Raptis et al. |
| 2012/0035432 A1 | 2/2012 | Katra et al. |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089412 A1 | 4/2012 | Bardy et al. |
| 2012/0089417 A1 | 4/2012 | Bardy et al. |
| 2012/0095352 A1 | 4/2012 | Tran |
| 2012/0101358 A1 | 4/2012 | Boettcher et al. |
| 2012/0101396 A1 | 4/2012 | Solosko et al. |
| 2012/0302906 A1 | 11/2012 | Felix et al. |
| 2013/0079611 A1 | 3/2013 | Besko |
| 2013/0085403 A1 | 4/2013 | Gunderson et al. |
| 2013/0096395 A1 | 4/2013 | Katra et al. |
| 2013/0116533 A1 | 5/2013 | Lian et al. |

(56) References Cited

U.S. PATENT DOCUMENTS

| | | |
|---|---|---|
| 2013/0123651 A1 | 5/2013 | Bardy |
| 2013/0158361 A1 | 6/2013 | Bardy |
| 2013/0225963 A1 | 8/2013 | Kodandaramaiah et al. |
| 2013/0243105 A1 | 9/2013 | Lei et al. |
| 2013/0274584 A1 | 10/2013 | Finlay et al. |
| 2013/0275158 A1 | 10/2013 | Fahey |
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2014/0012154 A1 | 1/2014 | Mazar et al. |
| 2014/0140359 A1 | 5/2014 | Kalevo et al. |
| 2014/0189928 A1 | 7/2014 | Oleson et al. |
| 2014/0206977 A1 | 7/2014 | Bahney et al. |
| 2015/0048836 A1 | 2/2015 | Guthrie et al. |
| 2015/0087951 A1* | 3/2015 | Felix ............... A61B 5/04085 600/382 |
| 2015/0165211 A1 | 6/2015 | Naqvi et al. |
| 2015/0177175 A1* | 6/2015 | Elder ............... G01N 27/3272 205/792 |
| 2015/0257670 A1 | 9/2015 | Ortega et al. |
| 2015/0359489 A1 | 12/2015 | Baudenbacher et al. |

FOREIGN PATENT DOCUMENTS

| | | |
|---|---|---|
| EP | 2438851 | 4/2012 |
| EP | 2438852 | 4/2012 |
| EP | 2465415 | 6/2012 |
| EP | 2589333 | 5/2013 |
| JP | H06319711 | 11/1994 |
| JP | 2004129788 | 4/2004 |
| WO | 0078213 | 12/2000 |
| WO | 03032192 | 4/2003 |
| WO | 2006009767 | 1/2006 |
| WO | 2006014806 | 2/2006 |
| WO | 2007066270 | 6/2007 |
| WO | 2007092543 | 8/2007 |
| WO | 2008010216 | 1/2008 |
| WO | 2008057884 | 5/2008 |
| WO | 2009036306 | 3/2009 |
| WO | 2009036327 | 3/2009 |
| WO | 2009112976 | 9/2009 |
| WO | 2009112978 | 9/2009 |
| WO | 2009112979 | 9/2009 |
| WO | 2009142975 | 11/2009 |
| WO | 2010066507 | 6/2010 |
| WO | 2011047207 | 4/2011 |
| WO | 2012140559 | 10/2012 |
| WO | 2012146957 | 11/2012 |

OTHER PUBLICATIONS 15 of the Hottest Wearable Gadgets, URL <http://thehottestgadgets.com/2008/09/the-15-hottest-wearable-gadgets-001253> (Web page cached on Sep. 27, 2008).

Alivecor's Heart Monitor for iPhone Receives FDA Clearance, URL <http://www.businesswire.com/news/home/20121203005545/en/AliveCor%E2%80%99s-Heart-Monitor-iPhone-Receives-FDA-Clearance#.U7rtq7FVTyF> (Dec. 3, 2012).

Bharadwaj et al., Techniques for Accurate ECG signal processing, EE Times, URL <www.eetimes.com/document.asp?doc_id=1278571> (Feb. 14, 2011).

Chen et al., "Monitoring Body Temperature of Newborn Infants at Neonatal Intensive Care Units Using Wearable Sensors," BodyNets 2010, Corfu Island, Greece. (Sep. 10, 2010).

Epstein, Andrew E. et al.; ACC/AHA/HRS 2008 Guidelines for Device-Based Therapy of Cardiac Rhythm Abnormalities. J. Am. Coll. Cardiol. 2008; 51; el-e62, 66 Pgs.

Fitbit automatically tracks your fitness and sleep, URL <http://www.fitbit.com/> (Web page cached on Sep. 10, 2008).

Smith, Kevin, "Jawbone Up VS. Fitbit Flex: Which Is The Best Fitness Band?" URL <http://www.businessinsider.com/fitbit-flex-vs-jawbone-up-2013-5?op=1> (Jun. 1, 2013).

Kligfield, Paul et al., Recommendations for the Standardization and Interpretation of the Electrocardiogram: Part I. J.Am.Coll. Cardiol; 2007; 49; 1109-27, 75 Pgs.

Lauren Gravitz, "When Your Diet Needs a Band-Aid, "Technology Review, MIT. (May 1, 2009).

Lieberman, Jonathan, "How Telemedicine is Aiding Prompt Ecg Diagnosis in Primary Care," British Journal of Community Nursing, vol. 13, No. 3, Mar. 1, 2008 (Mar. 1, 2008), pp. 123-126, XP009155082, ISSN: 1462-4753.

McManus et al., "A Novel Application for the Detection of an Irregular Pulse using an iPhone 4S in Patients with Atrial Fibrillation," vol. 10(3), pp. 315-319 (Mar. 2013).

Nike+ Fuel Band, URL <http://www.nike.com/us/en_us/c/nikeplus-fuelband> (Web page cached on Jan. 11, 2013).

P. Libby et al.,"Braunwald's Heart Disease—A Textbook of Cardiovascular Medicine," Chs. 11, pp. 125-148 and 12, pp. 149-193 (8th ed. 2008), American Heart Association.

Initial hands-on with Polar Loop activity tracker, URL <http://www.dcrainmaker.com/2013/09/polar-loop-firstlook.html> Sep. 17, 2013).

Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.

Sleepview, URL <http://www.clevemed.com/sleepview/overview.shtml> (Web pages cached on Feb. 23, 2010, Dec. 29, 2012 and Sep. 4, 2013).

Actigraphy/ Circadian Rhythm SOMNOwatch, URL <http://www.somnomedics.eu/news-events/publications/somnowatchtm.html> (Web page cached on Jan. 23, 2010).

Zio Event Card, URL <http://www.irhythmtech.com/zio-solution/zio-event/> (Web page cached on Mar. 11, 2013).

Zio Patch System, URL <http://www.irhythmtech.com/zio-solution/zio-system/index.html> (Web page cached on Sep. 8, 2013).

Seifert, Dan, "Samsung dives into fitness wearable with the Gear Fit/ The Verge," URL <http://www.theverge.com/2014/2/24/5440310/samsung-dives-into-fitness-wearables-with-the-gear-fit> (Feb. 24, 2014).

Soper, Taylor, "Samsung's new Galaxy S5 flagship phone has fingerprint reader, heart rate monitor," URL <http://www.geekwire.com/2014/samsung-galaxy-s5-fingerprint> (Feb. 24, 2014).

Dolcourt, Jessica, "See the Samsung Galaxy S5's Heart rate monitor in action," URL <http://www.cnet.com/news/see-the-samsung-galaxy-s5s-heart-rate-monitor-in-action> (Feb. 25, 2014).

Saadi et al. "Heart Rhythm Analysis Using ECG Recorded With a Novel Sternum Based Patch Technology—A Pilot Study." Cardio technix 2013—Proceedings of the International Congress on Cardiovascular Technologies, Sep. 20, 2013.

Anonymous. "Omegawave Launches Consumer App 2.0 in U.S. Endurance Sportswire—Endurance Sportswire." Jul. 11, 2013. URL:http://endurancesportswire.com/omegawave-launches-consumer-app-2-0-in-u-s/.

Chan et al. "Wireless Patch Sensor for Remote Monitoring of Heart Rate, Respiration, Activity, and Falls." pp. 5115-6118. 2013 35th Annual International Conference of the IEEE Engineering in Medical and Biology Society. Jul. 1, 2013.

Wei et al. "A Stretchable and Flexible System for Skin-Mounted Measurement of Motion Tracking and Physiological Signals." pp. 5772-5775. 2014 36th Annual International Conference of the IEEE Engineering in Medicine and Biology Society. Aug. 26, 2014.

Daoud et al. "Fall Detection Using Shimmer Technology and Multiresolution Analysis." Aug. 2, 2013. URL: https://decibel.ni.com/content/docs/DOC-26652.

Libbus. "Adherent Cardiac Monitor With Wireless Fall Detection for Patients With Unexplained Syncope." Abstracts of the First AMA-IEEE Medical Technology Conference on Individualized Healthcare. May 22, 2010.

Health Research—Hexoskin Biometric Shirt | Hexoskin URL:http://www.hexoskin.com/pages/health-research (Web page cached on Dec. 2, 2014).

(56) References Cited

OTHER PUBLICATIONS

Jacob Kastrenakes, "Apple Watch uses four sensors to detect your pulse," Sep. 9, 2014. URL: http://www.theverge.com/2014/9/9/6126991/apple-watch-four-back-sensors-detect-activity.
Nicole Lee, "Samsung Gear S review: an ambitious and painfully flawed smartwatch," Dec. 1, 2014. URL: http://www.engadget.com/2014/12/01/samsung-gear-s-review/.
A Voss et al., "Linear and Nonlinear Methods for Analyses of Cardiovascular Variability in Bipolar Disorders," Bipolar Disorders, votl. 8, No. 5p1, Oct. 1, 2006, pp. 441-452, XP55273826, DK ISSN: 1398-5647, DOI: 10.1111/.1399-56182006.00364.x.
"Varicrad-Kardi Software User's Manual Rev. 1.1", Jul. 8, 2009 (Jul. 8, 2009), XP002757888, retrieved from the Internet: URL:http://www.ehrlich.tv/KARDiVAR-Software.pdf [retrieved on May 20, 2016].
"Vedapulse UK," Jan. 1, 2014, XP002757887, Retrieved from the Internet: URL:http://www.vedapulseuk.com/diagnostic,/ [retrieved on May 19, 2016].
Duttweiler et al., "Probability Estimation in Arithmetic and Adaptive-Huffman Entropy Coders," IEEE Transactions on Image Processing. vol. 4, No. 3, Mar. 1, 1995, pp. 237-246.
Gupta et al., "An ECG Compression Technique for Telecardiology Application," India Conference (INDICON), 2011 Annual IEEE, Dec. 16, 2011, pp. 1-4.
Nave et al., "ECG Compression Using Long-Term Prediction," IEEE Transactions on Biomedical Engineering, IEEE Service Center, NY, USA, vol. 40, No. 9, Sep. 1, 1993, pp. 877-885.
Skretting et al., "Improved Huffman Coding Using Recursive Splitting," NORSIG, Jan. 1, 1999.

\* cited by examiner

METHOD FOR ADDRESSING MEDICAL CONDITIONS THROUGH A WEARABLE HEALTH MONITOR WITH THE AID OF A DIGITAL COMPUTER

FIELD

This application relates in general to wearable health monitors and, in particular, to a method for addressing medical conditions through a wearable health monitor with the aid of a digital computer.

BACKGROUND

Ensuring ready access to health care remains a pressing concern in our increasingly fast-paced society, but the ever climbing costs of health care makes having health insurance or similar financial arrangements all but essential for practically everyone except the wealthy or destitute. For the insured, the average health insurance carrier effectively serves as the gatekeeper that controls entry into the health care system and who manages the provisioning or denial of health care by stipulating the terms under which benefits will be paid. Thusly, health insurance subscribers (or enrollees) are at times caught in the middle between the dictates of their insurer and their ability to readily address their health concerns. On the one hand, a subscriber who bypasses his primary care provider, as typically required by an insurer as a first contact, and instead seeks out a medical specialist on his own may be taking a financial risk, as a health insurer could deny coverage. On the other hand, the primary care provider may not always offer a satisfactory or practicable solution, particularly in situations where a condition has symptoms that are transient or infrequent, or which underlies a disorder with a long incubatory or onset period, as can happen with certain chronic conditions.

For instance, cardiac rhythm disorders may present with lightheadedness, fainting, chest pain, hypoxia, syncope, palpitations, and congestive heart failure (CHF), yet cardiac rhythm disorders are often sporadic in occurrence and may not show up in-clinic during a conventional 12-second electrocardiogram (ECG). Moreover, some types of cardiac rhythm disorders may warrant immediate subspecialist care, such as heart blockage, tachycardia and bradycardia, which require the attention of an electrophysiologist. Continuous ambulatory ECG monitoring over an extended period is more apt to capture sporadic cardiac events, yet health insurers often require a primary care referral to a monitoring laboratory before underwriting long-term ECG monitoring and access to a specialist may be delayed or denied, depending upon the ECG monitoring results.

Notwithstanding, if a subscriber's ECG could be recorded in an ambulatory setting over a prolonged time period, particularly for as long as seven days or more, thereby allowing the subscriber to engage in activities of daily living, the chances of acquiring meaningful medical information and capturing an abnormal event while the subscriber is engaged in normal activities are vastly improved. Unfortunately, few, if any, options for long-term ambulatory ECG monitoring that a subscriber could undertake on his own are available, and existing ECG monitoring solutions require physician involvement with tacit insurer approval. For instance, Holter monitors are widely used for extended ECG monitoring, typically for 24-48 hour time periods. A typical Holter monitor is a wearable and portable version of an ECG and, as such, is cumbersome, expensive and typically available for use only through a prescription, which limits their usability, and the discretion to refer the subscriber still remains with the attending physician.

Similarly, the ZIO XT Patch and ZIO Event Card devices, manufactured by iRhythm Tech., Inc., San Francisco, Calif., are wearable monitoring devices that are typically worn on the upper left pectoral region to respectively provide continuous and looping ECG recording. The location is used to simulate surgically implanted monitors. The ZIO XT Patch device is limited to a 14-day period, while just the electrodes of the ZIO Event Card device can be worn for up to 30 days. Both devices represent compromises between length of wear and quality of ECG monitoring. Moreover, both of these devices are also prescription-only, which limits their usability and, the same as a Holter monitor, the discretion to refer the subscriber remains with the attending physician.

Therefore, a need remains for a low cost monitor for recording an ECG and other physiology that can be used by an individual on their own, without health insurance pre-authorization, yet which can identify and generate an actionable, health condition-specific (and ideally health insurance-payable) referral to a medical specialist when medically appropriate.

SUMMARY

Certain kinds of medical conditions, particularly conditions that only sporadically exhibit measurable symptoms, defy conventional forms of medical diagnosis centered on in-clinic testing. Individuals who suffer from such conditions can feel helpless in their attempts to secure access to medical care because, at least in part, they are left to the mercy of their condition to present symptoms at the right time to allow diagnosis and treatment. Moreover, such individuals may present to a physician or other health care provider unable to provide state-of-the-art care for cardiac conditions, especially cardiac rhythm disorders. Providing these individuals with ambulatory extended-wear health monitors that record ECG and physiology, preferably available over-the-counter and without health insurance preauthorization, is a first step towards addressing their needs expeditiously. In addition, these individuals need a way to gain entry into the health care system once a medically-actionable medical condition has been identified. Here, the ECG and physiology is downloaded and evaluated post-monitoring against medical diagnostic criteria. Medical specialists are pre-identified and paired up with key diagnostic findings, such that an individual whose monitoring data indicates a medical concern will be automatically referred and scheduled for a consultation, thereby removing delays and bypassing intermediaries who will not provide definitive interventions for the patient.

One embodiment provides a health monitoring apparatus for addressing medical conditions with the aid of a digital computer. A wearable health monitor includes an electrode patch having a plurality of electrodes provided to sense a patient's physiology and is adapted to be worn over a monitoring period. The wearable health monitor also includes a monitor recorder capable of recording the physiology throughout the monitoring period into an onboard memory. A download station includes an interface over which the physiology can be downloaded from the onboard memory of the wearable heath monitor upon completion of the monitoring period. A computer is adapted to be interfaced to the download station and includes a database including the physiology as retrieved from the download station and a medical diagnostic criteria. The computer also includes a processor and a memory configured to store code executable by the processor. A comparison module is configured to compare the physiology to the medical diagnostic criteria and to generate a diagnostic overread that comprises one or more diagnostic findings. A referral module is configured to determine the severity of any medical condition indicated by the diagnostic findings and to refer the patient to one or more pre-identified care providers via the computer for facilitated diagnosis as conditioned upon the severity of each such medical condition that exceeds a threshold tolerance level.

A further embodiment provides a method for addressing medical conditions through a wearable health monitor with the aid of a digital computer. A patient's physiology is sensed through a wearable health monitor adapted to be worn over a monitoring period. The physiology is recorded throughout the monitoring period into a memory onboard the wearable health monitor. The physiology is downloaded into a computer upon completion of the monitoring period and compared to a medical diagnostic criteria. A diagnostic overread is generated with the computer that includes one or more diagnostic findings. The severity of any medical condition indicated by the diagnostic findings is determined with the computer. The patient is referred to one or more pre-identified care providers via the computer for facilitated diagnosis as conditioned upon the severity of each such medical condition that exceeds a threshold tolerance level.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Figure 1:
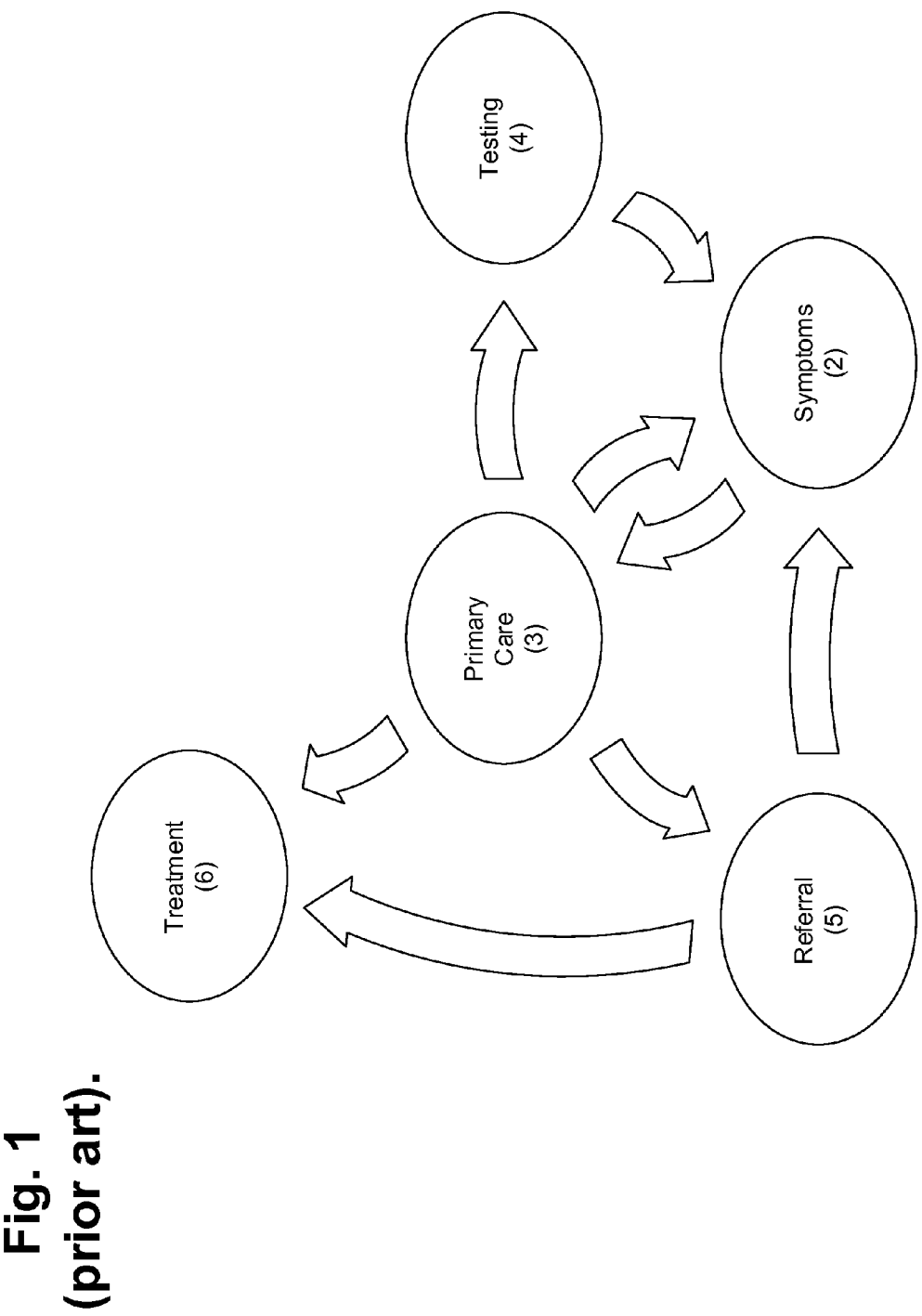
FIG. 1 is a process flow diagram showing, by way of example, one prior art approach to addressing medical conditions in a managed care model of health insurance.

For certain types of medical conditions, gaining access to health care can be a time-consuming and often frustrating experience. In the case of cardiac rhythm disorders, such delays can cause death. One possible reason stems from the restrictions often imposed on subscribers of both private and government mandated health insurance, especially when provided in the form of managed care, which employs a network of contracted health care providers and medical facilities that are structured to control costs and help to improve overall quality of care. FIG. 1 is a process flow diagram showing, by way of example, one prior art approach to addressing medical conditions in a managed care model 1 of health insurance. In this model, the average health insurance carrier, such as those provided by the Affordable Care Act, effectively serves as the gatekeeper that controls entry into the health care system and who manages the provisioning or denial of health care by stipulating the terms under which benefits will be paid. At times, the goals of the health insurer as the arbiter of benefits can be at odds with the medical concerns of their subscribers, who are generally expected to comply with their insurer's guidelines to receive care for non-urgent health conditions, or to seek an exception, preferably beforehand.

The managed care model 1 of health insurance can work well in providing access to care for those subscribers who are able to be served by the network of health care providers and facilities that has been set up by the health insurer to address the majority of expected health concerns. For example, for non-urgent, undiagnosed physical ailments and health conditions, a health insurer will generally require a subscriber suffering symptoms (step 2) to see their primary care provider first (step 3). The subscriber may undergo testing (step 4) and follow up with the primary care provider (step 3) with the expectation that most health conditions can be resolved without departing from the primary care level. When circumstances dictate, the subscriber may be referred to a medical specialist (step 5); ordinarily, a showing of medical necessity will be required before the health insurer will be contractually obligated to pay benefits. The type of medical specialist to whom the subscriber is referred is based upon the primary care provider's understanding of the health condition, experience, and referral network, which may be biased towards the health care provider network already set in place. At its best, such a system may still cause considerable delays in diagnosis and management of a cardiac rhythm disorder or other serious physiological condition.

The managed care model 1 can begin to fail when health insurance subscribers encounter medical conditions that depart from the expected norm, particularly medical conditions whose symptoms are transient or infrequent, or which underlie a disorder with a long incubatory or onset period, such as heart disease, diabetes mellitus, epilepsy, Parkinson's disease, and Alzheimer's disease. The cycle of having symptoms (step 2), seeing a primary care provider (step 3), undergoing testing (step 4), and perhaps receiving a medical specialist referral (step 5) may be repeated several times until the health condition either resolves on its own (step 2), is diagnosed and treated at the primary care level (step 3), or possibly worsens, perhaps significantly, such that intervention by a medical specialist is necessary (step 6), albeit at the cost of potentially complicating treatment, endangering cure or effective management, increasing medical costs, and negatively affecting quality or duration of life.

In these situations, access to care is hindered, at least in part, by the difficulty of or inability to narrow down the cause of the symptoms through in-clinic testing. Repetitions of the primary care cycle may not always be efficacious; for example, in-clinic testing of a subscriber is only effective if administered coincident to the timely occurrence of a sporadically-occurring medical condition, yet such conditions, such as an abnormal heart rhythm or syncope, rarely occur on demand or when needed for present diagnosis. In addition, some health conditions may require a level of care or medical specialization with which the primary care provider is unversed, and a referral may not provide the relief ultimately sought. In some situations, the cycle of testing and follow up may be repeatedly revisited; the subscriber may be forced to undergo more testing and delay until and if an appropriate medical specialist becomes involved. Misdiagnosis or maldiagnosis remain potential risks.

As an example, consider the potentially life-threatening problem of syncope, or loss of consciousness. Syncope affects millions of Americans annually. Syncope also can be extremely difficult to diagnose because the condition is intermittent and gives no warning. Causes can range from the relatively trivial, such as fainting from emotional excitement, to a life-threatening cardiac rhythm disorder, like transient heart block, that if the condition were to persist, would result in death, and not just transient loss of consciousness. Atrial fibrillation, another potential cause of syncope, is extremely common and is an occult and leading cause of stroke. Most patients with syncope never see a physician because they either dismiss the condition as a one-time event, rationalizing its import away, or struggle to see a physician of some sort, almost always a generalist, for help. Many such physicians either inappropriately dismiss the patient as anxious or begin the long-process to getting at the root cause. At minimum, this process requires referral to a cardiologist, who then prescribes an ECG monitor, usually the traditional 24-hour Holter monitor, which in turn must be interpreted. The patient must then return for evaluation and possible therapy. The delay for each of these steps can take weeks. Often, the patient (or sometimes the doctor) gives up and returns to his "normal" life only to experience a second episode of syncope or something worse, like a stroke or death. The better way to deal with syncope is for the patient to self-apply an over-the-counter ECG monitor at modest personal expense, yielding valuable data in a fraction of the time and cost of the traditional approach, potential preventing a stroke or even saving the patient's life.

The shortcomings of the managed care model 1, as well as other types of health care provisioning arrangements that mandate who an individual must see first for non-urgent, undiagnosed medical conditions, can be significantly overcome by empowering the patient with basic self-help tools that improve access to health care. These tools include the ability to perform self-monitoring of personal physiology, including ECG monitoring, as described in the previous paragraph, and to be able to tap into an automated referral network that, when medically appropriate, will connect the individual with the right specialist for the medical conditions observed and diagnosed. Such physiological monitoring can be provided through a wearable monitor that can be interfaced with a diagnostics computer system that can download physiology recorded by the wearable monitor and generate a medically-actionable diagnostic overread, all without requiring the constant oversight or active involvement of a health insurer or managed care system.

Figure 2:
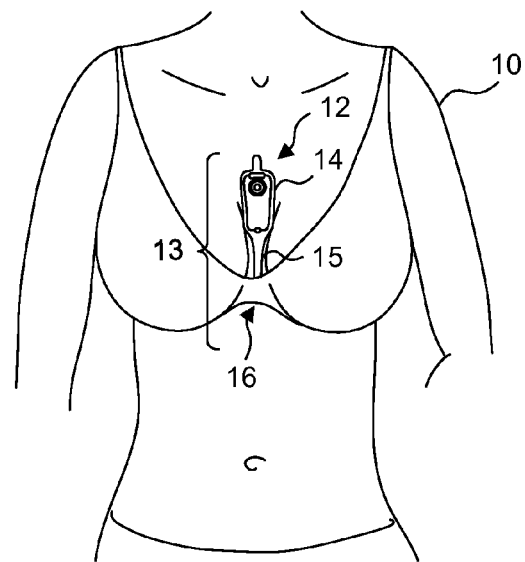
FIGS. 2 and 3 are diagrams showing, by way of examples, an extended wear electrocardiography and physiological wearable monitor respectively fitted to the sternal region of a female patient and a male patient.
Figure 3:
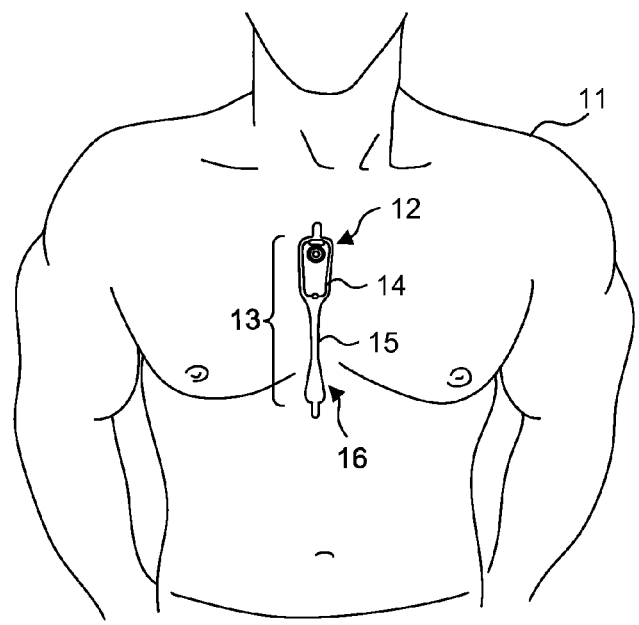

By way of example, using the heretofore referenced problem of syncope resulting from a cardiac rhythm disorder, the wearable monitor includes two components, a flexible extended wear electrode patch and a removable reusable monitor recorder. FIGS. 2 and 3 are diagrams showing, by way of example, an extended wear electrocardiography and physiological wearable monitor 12, including a monitor recorder 14 in accordance with one embodiment, respectively fitted to the sternal region of a female patient 10 and a male patient 11. Both the monitor recorder 14 and the electrode patch 15 are optimized to capture electrical signals from the propagation of low amplitude, relatively low frequency content cardiac action potentials, particularly the P-waves generated during atrial activation. The wearable monitor 12 could include additional sensors to monitor and record other types of physiology, including blood pressure, respiratory rate, temperature, and blood glucose, either in addition to or in lieu of heart rate.

The wearable monitor 12 sits centrally (in the midline) on the patient's chest over the mid-sternum 13 oriented top-to-bottom with the monitor recorder 14 preferably situated towards the patient's head. The electrode patch 15 is shaped to fit comfortably, conforming to the contours of the patient's chest approximately centered on the sternal midline 16 (or immediately to either side of the sternum 13). The distal end of the electrode patch 15 extends towards the xiphoid process and, depending upon the patient's build, may straddle the region over the xiphoid process. The proximal end of the electrode patch 15, located under the monitor recorder 14, is below the manubrium and, depending upon patient's build, may straddle the region over the manubrium.

During ECG monitoring, the amplitude and strength of action potentials sensed on the body's surface are affected to varying degrees by cardiac, cellular, and extracellular structure and activity, vector of current flow, and physical factors, like obesity, dermatitis, large breasts, and high impedance skin, as can occur in dark-skinned individuals. Sensing along the sternal midline 16 (or immediately to either side of the sternum 13) significantly improves the ability of the wearable monitor 12 to cutaneously sense cardiac electric signals, particularly the P-wave (or atrial activity) and, to a lesser extent, the QRS interval signals in the ECG waveforms that indicate ventricular activity by countering some of the effects of these factors, such as described in commonly-assigned U.S. patent application, entitled "Ambulatory Electrocardiography Monitoring Patch Optimized for Capturing Low Amplitude Cardiac Action Potential Propagation," Ser. No. 14/488,230, filed Sep. 16, 2014, pending, the disclosure of which is incorporated by reference, while simultaneously facilitating comfortable long-term wear for many weeks. The sternum 13 overlies the right atrium of the heart and the placement of the wearable monitor 12 in the region of the sternal midline 16 puts the ECG electrodes of the electrode patch 15 in a location better adapted to sensing and recording P-wave signals than other placement locations, say, the upper left pectoral region or lateral thoracic region or the limb leads. In addition, placing the lower or inferior pole (ECG electrode) of the electrode patch 15 over (or near) the xiphoid process facilitates sensing of ventricular activity and provides excellent recordation of the QRS interval as the xiphoid process overlies the apical region of the ventricles.

Figure 4:
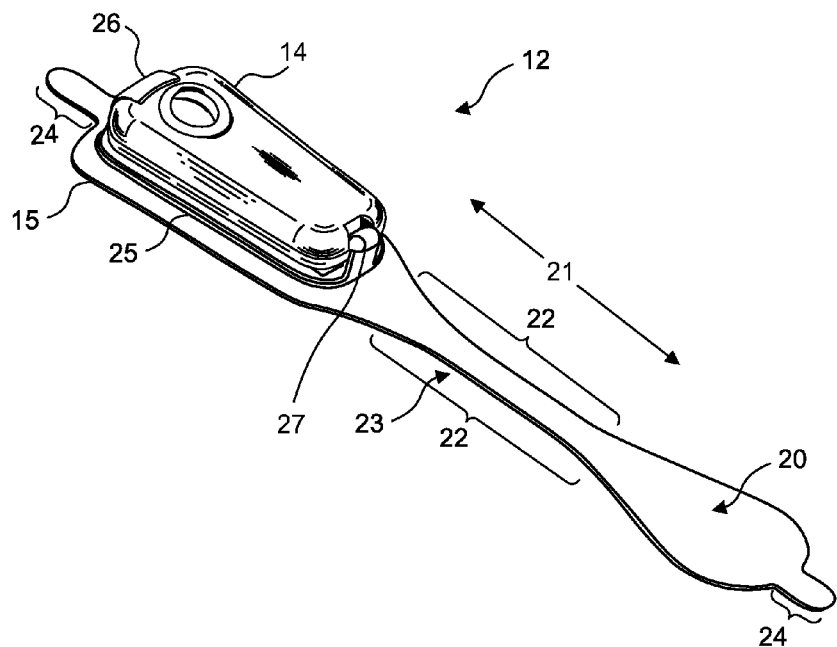
FIG. 4 is a perspective view showing a contact-activated extended wear electrode patch with a monitor recorder inserted.

During use, the electrode patch 15 is first adhered to the skin along the sternal midline 16 (or immediately to either side of the sternum 13). A monitor recorder 14 is then snapped into place on the electrode patch 15 to initiate ECG monitoring, with the monitoring being initiated upon the recorder 14 detecting contact with the patient. (Note that the monitor can also be snapped into place on a table prior to removing adhesive liner and application of the electrode patch to the skin.) FIG. 4 is a perspective view showing a contact-activated extended wear electrode patch 15 with a monitor recorder 14 inserted. The body of the electrode patch 15 is preferably constructed using a flexible backing 20 formed as an elongated strip 21 of wrap knit or similar stretchable material with a narrow longitudinal mid-section 23 evenly tapering inward from both sides. A pair of cut-outs 22 between the distal and proximal ends of the electrode patch 15 create a narrow longitudinal midsection 23 or "isthmus" and defines an elongated "hourglass"-like shape, when viewed from above. The upper part of the "hourglass" is sized to allow an electrically non-conductive receptacle 25, sits on top of the outward-facing surface of the electrode patch 15, to be affixed to the electrode patch 15 with an ECG electrode placed underneath on the patient-facing underside, or contact, surface of the electrode patch 15; the upper part of the "hourglass" has a longer and wider profile (but still rounded and tapered to fit comfortably between the breasts) than the lower part of the "hourglass," which is sized primarily to allow just the placement of an ECG electrode of appropriate shape and surface area to record the P-wave and the QRS signals sufficiently given the inter-electrode spacing.

The electrode patch 15 incorporates features that significantly improve wearability, performance, and patient comfort throughout an extended monitoring period for men or women. During wear, the electrode patch 15 is susceptible to pushing, pulling, and torqueing movements, including compressional and torsional forces when the patient bends forward, and tensile and torsional forces when the patient leans backwards or twists their thorax. To counter these stress forces, the electrode patch 15 incorporates strain and crimp reliefs, such as described in commonly-assigned U.S. patent application Publication No. 2015/0087948, published Mar. 26, 2015, pending, and U.S. patent application, entitled "Extended Wear Electrocardiography Patch," Ser. No. 14/736,257, filed Jun. 16, 2015, pending, the disclosures of which are incorporated by reference. In addition, the cut-outs 22 and longitudinal midsection 23 help minimize interference with and discomfort to breast tissue, particularly in women (and gynecomastic men). The cut-outs 22 and longitudinal midsection 23 further allow better conformity of the electrode patch 15 to sternal bowing and to the narrow isthmus of flat skin that can occur along the bottom of the intermammary cleft between the breasts, especially in buxom women. The cut-outs 22 and longitudinal midsection 23 help the electrode patch 15 fit nicely between a pair of female breasts in the intermammary cleft. Still other shapes, cut-outs and conformities to the electrode patch 15 are possible.

The monitor recorder 14 removably and reusably snaps into an electrically non-conductive receptacle 25 during use. The monitor recorder 14 contains electronic circuitry for recording and storing the patient's electrocardiography as sensed via a pair of ECG electrodes provided on the electrode patch 15, such as described in commonly-assigned U.S. Patent Application Publication No. 2015/0087949, published Mar. 26, 2015, pending, the disclosure which is incorporated by reference. The non-conductive receptacle 25 is provided on the top surface of the flexible backing 20 with a retention catch 26 and tension clip 27 molded into the non-conductive receptacle 25 to conformably receive and securely hold the monitor recorder 14 in place.

Figure 5:
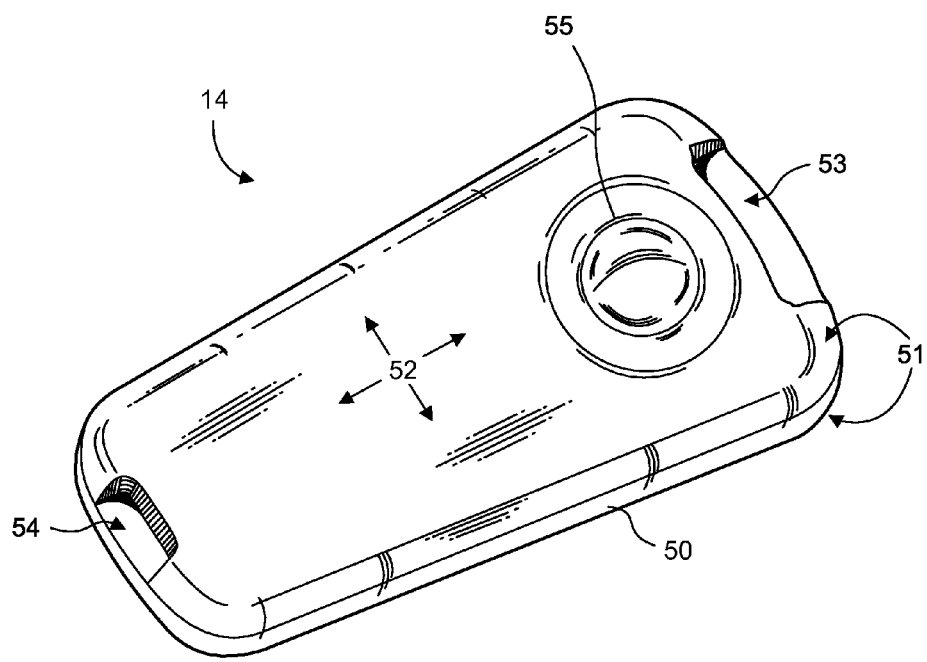
FIG. 5 is a perspective view showing the monitor recorder of FIG. 4.

The monitor recorder 14 includes a sealed housing that snaps into place in the non-conductive receptacle 25. FIG. 5 is a perspective view showing the monitor recorder 14 of FIG. 4. The sealed housing 50 of the monitor recorder 14 has a rounded isosceles trapezoidal-like shape 52, for comfort with women, when viewed from above, such as described in commonly-assigned U.S. Design Pat. No. D717,955, entitled "Electrocardiography Monitor," issued Nov. 18, 2014, the disclosure of which is incorporated by reference. In addition, a label, barcode, QR code, or other visible or electronic indicia can be printed on the outside of, applied to the outside of, or integrated into the sealed housing 50 to uniquely identify the monitor recorder 14 and can include a serial number, manufacturing lot number, date of manufacture, and so forth. The edges 51 along the top and bottom surfaces are rounded for patient comfort. The sealed housing 50 is approximately 47 mm long, 23 mm wide at the widest point, and 7 mm high, excluding a patient-operable tactile-feedback button 55. The sealed housing 50 can be molded out of polycarbonate, ABS, or an alloy of those two materials. The button 55 is waterproof and the button's top outer surface is molded silicon rubber or similar soft pliable material. A retention detent 53 and tension detent 54 are molded along the edges of the top surface of the housing 50 to respectively engage the retention catch 26 and the tension clip 27 molded into non-conductive receptacle 25. Other shapes, features, and conformities of the sealed housing 50 are possible.

The electrode patch 15 is intended to be disposable. The monitor recorder 14, however, is reusable and can be transferred to successive electrode patches 15 to ensure continuity of monitoring. The placement of the wearable monitor 12 in a location at the sternal midline 16 (or immediately to either side of the sternum 13) benefits long-term extended wear by removing the requirement that ECG electrodes be continually placed in the same spots on the skin throughout the monitoring period. Instead, the patient is free to place an electrode patch 15 anywhere within the general region of the sternum 13.

As a result, at any point during ECG monitoring, the patient's skin is able to recover from the wearing of an electrode patch 15, which increases patient comfort and satisfaction, while the monitor recorder 14 ensures ECG monitoring continuity with minimal effort. A monitor recorder 14 is merely unsnapped from a worn out electrode patch 15, the worn out electrode patch 15 is removed from the skin, a new electrode patch 15 is adhered to the skin, possibly in a new spot immediately adjacent to the earlier location, and the same monitor recorder 14 is snapped into the new electrode patch 15 to reinitiate and continue the ECG monitoring.

Figure 6:
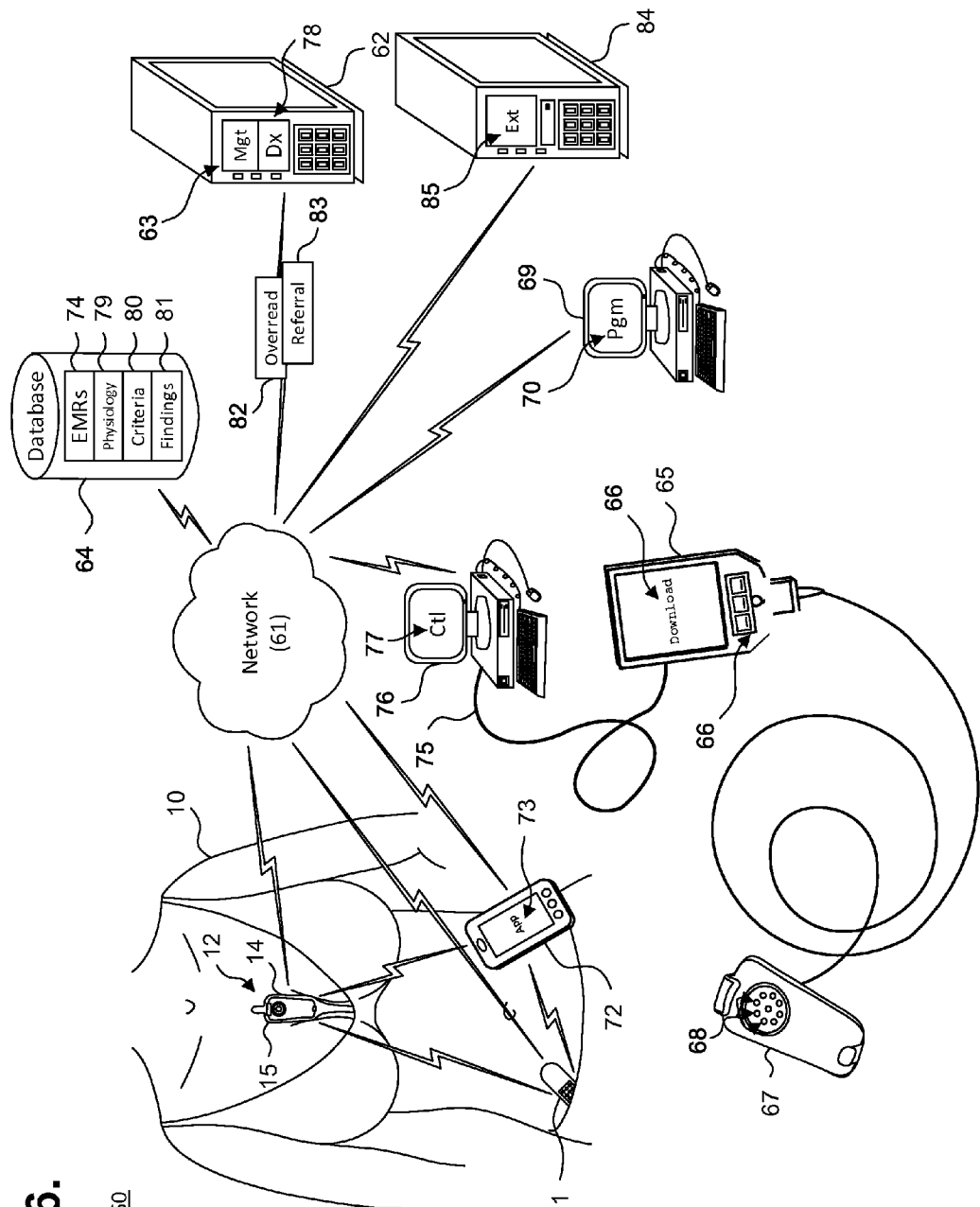
FIG. 6 is a functional block diagram showing a system for addressing medical conditions with the aid of a digital computer through the monitor recorder of FIG. 4, in accordance with one embodiment.

When operated standalone, the monitor recorder 14 senses and records the patient's ECG and physiology data into an onboard memory, which can be downloaded and evaluated to identify and generate an actionable, health condition-specific (and ideally health insurance-payable) referral to a medical specialist when medically appropriate. In addition, the wearable monitor 12 can interoperate with other devices, which further improves upon a patient's ability to address medical conditions on his own. FIG. 6 is a functional block diagram showing a system 60 for addressing medical conditions with the aid of a digital computer 62 through the monitor recorder 14 of FIG. 4, in accordance with one embodiment. In one form, the monitor recorder 14 is a reusable component that can be fitted during patient monitoring into a non-conductive receptacle provided on the electrode patch 15, and later removed for offloading of stored ECG data or to receive revised programming. The monitor recorder 14 can then be connected to a download station 65, which could be a dedicated programmer or other device, including a digital computer, such as personal computer 76, that permits the retrieval of stored ECG monitoring data, execution of diagnostics on or programming of the monitor recorder 14, or performance of other functions.

To facilitate physical connection with a download station 65, the monitor recorder 14 has a set of electrical contacts (not shown) that enable the monitor recorder 14 to physically interface to a set of terminals 68 on a paired receptacle 67 of the download station 65. In turn, the download station 65 executes a communications or offload program 66 ("Offload") or similar program that interacts with the monitor recorder 14 via the physical interface to retrieve the stored ECG and physiology monitoring data. The download station 65 could be a server, personal computer, such as personal computer 76, tablet or handheld computer, smart mobile device, or purpose-built device designed specific to the task of interfacing with a monitor recorder 14. Still other forms of download station 65 are possible. In a further embodiment, the data from the monitor 12 can be offloaded wirelessly and the monitor 12 can interface with the download station 65 wirelessly.

The ECG and physiology data retrieved from the monitor recorder 14 by the download station 65 can, in turn, be retrieved from the download station 65 over a hard link 75 using a control program 77 ("Ctl") or analogous application executing on a personal computer 76 or other connectable computing device, via a communications link (not shown), whether wired or wireless, or by physical transfer of storage media (not shown). The personal computer 76 or other connectable device may also execute middleware that converts ECG and physiology data and other information into a format suitable for use by a third-party post-monitoring analysis program. Formatted data stored on the personal computer 76 is maintained and safeguarded in the same manner as electronic medical records (EMRs) 74 are protected in the secure database 64, as further discussed infra. In a further embodiment, the download station 65 is able to directly interface with other devices over a computer communications network 61, which could be some combination of a local area network and a wide area network, including the Internet or another telecommunications network, over a wired or wireless connection.

A client-server model could be used for ECG and physiology data download and analysis. In this model, a server 62 remotely interfaces with the download station 65, by way of the personal computer 76, over the network 61 and retrieves the formatted data or other information. The server 62 executes a patient management program 63 ("Mgt") or similar application that stores the retrieved formatted data and other information in a secure database 64 cataloged in that patient's EMRs 74. Patients' EMRs can be supplemented with other information, such as medical history, testing results, and so forth, which can be factored into automated diagnosis and referral. In addition, the patient management program 63 could manage a subscription service that authorizes a monitor recorder 14 to operate for a set period of time or under pre-defined operational parameters.

The patient management program 63, or other trusted application, also maintains and safeguards the secure database 64 to limit access to patient EMRs 74 to only authorized parties for appropriate medical or other uses, such as mandated by state or federal law, such as under the Health Insurance Portability and Accountability Act (HIPAA) or per the European Union's Data Protection Directive. For example, a physician may seek to review and evaluate his patient's ECG monitoring data, as securely stored in the secure database 64. The physician would execute an application program 70 ("Pgm"), such as a post-monitoring ECG analysis program, on a personal computer 69 or other connectable computing device, and, through the application program 70, coordinate access to his patient's EMRs 74 with the patient management program 63. Other schemes and safeguards to protect and maintain the integrity of patient EMRs 74 are possible.

In a further embodiment, the wearable monitor 12 can interoperate wirelessly with other wearable physiology monitors and activity sensors 71, such as activity trackers worn on the wrist or body, and with mobile devices 72, including smart watches and smartphones. Wearable physiology monitors and activity sensors 71 encompass a wide range of wirelessly interconnectable devices that measure or monitor a patient's physiological data, such as heart rate, temperature, blood pressure, respiratory rate, blood pressure, blood sugar (with appropriate subcutaneous probe), oxygen saturation, minute ventilation, and so on; physical states, such as movement, sleep, footsteps, and the like; and performance, including calories burned or estimated blood glucose level. The physiology sensors in non-wearable mobile devices, particularly smartphones, are generally not meant for continuous tracking and do not provide medically precise and actionable data sufficient for a physician to prescribe a surgical or serious drug intervention; such data can be considered screening information that something may be wrong, but not data that provides the highly precise information that may allow for a surgery, such as implantation of a pacemaker for heart block or a defibrillator for ventricular tachycardia, or the application of serious medications, like blood thinners for atrial fibrillation or a cardiac ablation procedure. Such devices, like smartphones, are better suited to pre- and post-exercise monitoring or as devices that can provide a signal that something is wrong, but not in the sufficient detail and medico-legal validation to allow for medical action. Conversely, medically actionable wearable sensors and devices sometimes provide continuous recording for relatively short time periods, but must be paired with a smartphone or computer to offload and evaluate the recorded data, especially if the data is of urgent concern, such as mobile cardiac outpatient telemetry devices.

Wearable physiology monitors and activity sensors 71, also known as "activity monitors," and to a lesser extent, "fitness" sensor-equipped mobile devices 72, can trace their life-tracking origins to ambulatory devices used within the medical community to sense and record traditional medical physiology that could be useful to a physician in arriving at a patient diagnosis or clinical trajectory, as well as from outside the medical community, from, for instance, sports or lifestyle product companies who seek to educate and assist individuals with self-quantifying interests. Data is typically tracked by the wearable physiology monitors or activity sensors 71 and mobile device 72 for only the personal use of the wearer. The physiological monitoring is usually considered informational only, even where a device originated within the medical or health care community, in part, because the data has not been (and is not intended to be) time-correlated to physician-supervised monitoring. Importantly, medically-significant events, such as cardiac rhythm disorders, including tachyarrhythmias, like ventricular tachycardia or atrial fibrillation, and bradyarrhythmias, like heart block, while potentially detectable with the appropriate diagnostic heuristics, are neither identified nor acted upon by the wearable physiology monitors and activity sensors 71 and the mobile device 72. Nevertheless, wearable physiology monitors or activity sensors 71 and mobile device 72 may play a role in helping a patient start to address a medical concern at a lay level.

Frequently, wearable physiology monitors and activity sensors 71 are capable of wirelessly interfacing with mobile devices 72, particularly smart mobile devices, including so-called "smartphones" and "smart watches," as well as with personal computers and tablet or handheld computers, to download monitoring data either in real-time or in batches. The wireless interfacing of such activity monitors is generally achieved using transceivers that provide low-power, short-range wireless communications, such as Bluetooth, although some wearable physiology monitors and activity sensors 71, like their mobile device cohorts, have transceivers that provide true wireless communications services, including 4G or better mobile telecommunications, over a telecommunications network. Other types of wireless and wired interfacing are possible.

Where the wearable physiology monitors and activity sensors 71 are paired with a mobile device 72, the mobile device 72 executes an application ("App") that can retrieve the data collected by the wearable physiology monitor and activity sensor 71 and evaluate the data to generate information of interest to the wearer, such as an estimation of the effectiveness of the wearer's exercise efforts. Where the wearable physiology monitors and activity sensors 71 has sufficient onboard computational resources, the activity monitor itself executes an app without the need to relay data to a mobile device 72. Generally, such more computationally-capable wearable physiology monitors and activity sensors are also equipped with wireless communications services transceivers, such as found in some smart watches that combine the features of activity monitors with mobile devices. Still other activity monitor and mobile device functions on the collected data are possible.

In a further embodiment, a wearable physiology monitor, activity sensor 71, or mobile device 72 worn or held by the patient 10, or otherwise be used proximal to the patient's body, can be used to first obtain and then work collaboratively with a more definitive (medical grade) monitor recorder 14 to enable the collection of physiology by the monitor recorder 14 before, during, and after potentially medically-significant events. The wearable physiology monitor, activity sensor 71, or mobile device 72 must be capable of sensing cardiac activity, particularly heart rate or rhythm, or other types of physiology or measures, either directly or upon review of relayed data. Where the wearable physiology monitor or activity sensor 71 is paired with a mobile device 72, the mobile device 72 serves as a relay device and executes an application that will trigger the dispatch of a monitor recorder 14 to the patient 10 upon detecting potentially medically-significant events in the data provided by the paired activity monitor, such as cardiac rhythm disorders, including tachyarrhythmias and bradyarrhythmias, which are readily identifiable respectively based on abnormally rapid or slow heart rate. If the mobile device 72 is itself performing the monitoring of the patient's physiology, the mobile device 72 executes an application that will trigger the dispatch of a monitor recorder 14 to the patient 10 in near-real time upon detecting potentially medically-significant events, thereby avoiding the delay incurred by data relay from an activity monitor. Finally, if the wearable physiology monitor or activity sensor 71 has sufficient onboard computational resources and also is equipped with a wireless communications services transceiver, the wearable physiology monitor or activity sensor 71 effectively becomes the mobile device 72 and executes an application that will trigger the dispatch of a monitor recorder 14 to the patient 10 in near-real time upon detecting potentially medically-significant events without the need to first interface with a mobile device 72. Still other configurations of the detection application are possible.

The act of triggering the dispatch of a monitor recorder 14 represents the first step in a cascade of possible medical interventions of potentially increasing seriousness and urgency. Sensors 71 and devices 73 are generally considered not to be capable of detecting and recording medically precise and actionable data, whereas, as a device designed and approved for extended wear, the monitor recorder 14 continually monitors the patient's physiology over a long time period and will capture any medically-actionable data leading up to, throughout the occurrence of, and following an event of potential medical concern.

The monitoring data recorded by the monitor recorder 14 can be uploaded directly into the patient's EMRs 74, either by using a mobile device 72 as a conduit for communications with a server 62 coupled to a secure database 64 within which the patient's EMRs 74 are stored, or directly to the server 62, if the monitor recorder 14 is appropriately equipped with a wireless transceiver or similar external data communications interface, as further described infra. Thus, the data recorded by the monitor recorder 14 would directly feed into the patient's EMRs 74, thereby allowing the data to be made certifiable for immediate use by a physician or healthcare provider. No intermediate steps would be necessary when going from cutaneously sensing cardiac electric signals and collecting the patient's physiology using a monitor recorder 14 to presenting that recorded data to a physician or healthcare provider for medical diagnosis and care. The direct feeding of data from the monitor recorder 14 to the EMRs 74 clearly establishes the relationship of the data, as recorded by the monitor recorder 14, to the patient 10 that the physician is seeing and appropriately identifies any potentially medically-significant event recorded in the data as originating in the patient 10 and nobody else.

Based on the monitoring ECG and physiology data, physicians and healthcare providers can rely on the data as certifiable and can directly proceed with determining the appropriate course of treatment for the patient 10, including undertaking further medical interventions as appropriate. The server 62 executes a patient diagnosis program 78 ("Dx") or similar application that can evaluate the recorded physiology 79, as fed into the patient's EMRs 74. The patient diagnosis program 78 compares the recorded physiology 79 of each patient to a set of medical diagnostic criteria 80, from which a diagnostic overread 82 is generated. Each diagnostic overread 82 includes one or more diagnostic findings 81 that are rated by degree of severity. If at least one of the diagnostic findings 81 for a patient exceed a threshold level of tolerance, which may be tailored to a specific client, disease or medical condition group, or applied to a general patient population, a referral 83, which can include orders to seek immediate treatment, is generated on behalf of the patient to a pre-identified care provider for medical care and the patient is notified.

The referral 83 is an actionable, health condition-specific form of communication that is electronically dispatched directly to a care provider. The care provider is reached through a care provider network server 84, or other patient referral system, that executes an external patient care program ("Ext") and which interfaces over the network 61 to the patient diagnosis program 78 executing on the server 62. In a further embodiment, the care provider and patient could also be reached using social media, provided the necessary patient privacy permissions are in place. The referral 83 represents a request on behalf of the patient to an appropriate type of care provider, which could be a general practice physician if the patient's physiology 79 represents normal tracings or a medical specialist, for instance, a cardiac electrophysiologist referral when the physiology 79 includes a diagnostic finding 81 of an event of sufficient potential severity to warrant the possible implantation of a pacemaker for heart block or a defibrillator for ventricular tachycardia. A further example would be the direct referral to a cardiologist for the finding of atrial fibrillation for the initiation of blood thinners and possibly an ablation procedure.

Other uses of the data recorded by the monitor recorder 14 and other devices are possible. For instance, a patient 10 who has previously suffered heart failure is particularly susceptible to ventricular tachycardia following a period of exercise or strenuous physical activity. A wearable sensor 71 or device 73 that includes a heart rate monitor would be able to timely detect an irregularity in heart rhythm. The application executed by the sensor 71 or device 73 allows those devices to take action by triggering the dispatch of a monitor recorder 14 to the patient 10, even though the data recorded by the sensor 71 or device 73 is itself generally medically-insufficient for purposes of diagnosis and care. Thus, rather than passively recording patient data, the sensor 71 or device 73 takes on an active role in initiating the provisioning of medical care to the patient 10 and starts a cascade of appropriate medical interventions under the tutelage of and followed by physicians and trained healthcare professionals.

In a still further embodiment, the monitor recorder 14 could upload an event detection application to the sensor 71 or device 73 to enable those devices to detect those types of potentially medically-significant events, which would trigger the dispatch of a monitor recorder 14 to the patient 10. Alternatively, the event detection application could be downloaded to the sensor 71 or device 73 from an online application store or similar online application repository. Finally, the monitor recorder 14 could use the sensor 71 or device 73 to generate an appropriate alert, including contacting the patient's physician or healthcare services, via wireless (or wired) communications, upon detecting a potentially medically-significant event or in response to a patient prompting.

The patient 10 could be notified by the sensor 71 or device 73, through the sensor's or device's user interface, that an event of potential medical concern has been detected coupled with an offer to have a monitor recorder 14 sent out to the patient 10, assuming that the patient 10 is not already wearing a monitor recorder 14. Alternatively, the sensor 71 or device 73 could unilaterally send out a request for a monitor recorder 14. The request for a monitor recorder 14 could be sent via wireless (or wired) communications to the patient's physician, a medical service provider organization, a pharmacy, an emergency medical service, or other appropriate healthcare entity that would, in turn, physically provide the patient with a monitor recorder 14. The patient 10 could also be told to pick up a monitor recorder 14 directly from one of the above-identified sources.

Conventional Holter monitors, as well as the ZIO XT Patch and ZIO Event Card devices, described supra, are currently available only by a physician's prescription for a specific patient 10. As a result, the physiological data recorded by these monitors and devices are assumed by healthcare professional to belong to the patient 10. In this prescriptive medicine context, grave questions as to the authenticity of the patient's identity and the data recorded do not generally arise, although current medical practice still favors requesting affirmative patient and caregiver identification at every step of healthcare provisioning. As a device intended for adoption and usage broader than prescriptive medicine, the monitor recorder 14 carries the potential to be used by more than one individual, which can raise concerns as to the veracity of the data recorded.

In a still further embodiment, the mobile device 72, or, if properly equipped, the activity monitor, can be used to help authenticate the patient 10 at the outset of and throughout the monitoring period. The mobile device 72 (or activity monitor) must be appropriately equipped with a digital camera or other feature capable of recording physical indicia located within the proximity of the mobile device 72. For instance, the Samsung Galaxy S5 smartphone has both a biometric fingerprint reader and autofocusing digital camera built in. Upon receipt of a monitor recorder 14, the patient 10 can use the photographic or other recording features of the mobile device 72 (or activity monitor) to physically record the placement and use of the monitor recorder 14. For instance, the patient 10 could take a picture or make a video of the monitor recorder 14 using as applied to the chest using the built-in digital camera. The patient 10 could also swipe a finger over the biometric fingerprint reader. Preferably, the patient 10 would include both his or her face or similar uniquely-identifying marks or indicia, such as a scar, tattoo, body piercing, or RFID chip, plus any visible or electronic indicia on the outside of the monitor recorder's housing, as further described infra with reference to FIG. 5, in the physical recording. The physical recording would then be sent by the mobile device 72 (or activity monitor) via wireless (or wired) communications to the patient's physician's office or other appropriate caregiver, thereby facilitating the authentication of the data recorded by the monitor recorder 14. Alternatively, the physical recording could be securely stored by the monitor recorder 14 as part of the monitoring ECG and physiology data set.

The mobile device 72 could also serve as a conduit for providing the data collected by the wearable physiology monitor or activity sensor 71 to the server 62, or, similarly, the wearable physiology monitor or activity sensor 71 could itself directly provide the collected data to the server 62. The server 62 could then merge the collected data into the wearer's EMRs 74 in the secure database 64, if appropriate (and permissible), or the server 62 could perform an analysis of the collected data, perhaps based by comparison to a population of like wearers of the wearable physiology monitor or activity sensor 71. Still other server 62 functions on the collected data are possible.

Finally, the monitor recorder 14 can also be equipped with a wireless transceiver. Thus, when wireless-enabled, both wearable physiology monitors, activity sensors 71, and mobile devices 72 can wirelessly interface with the monitor recorder 14, which could either provide data or other information to, or receive data or other information from an interfacing device for relay to a further device, such as the server 62, analysis, or other purpose. In addition, the monitor recorder 14 could wirelessly interface directly with the server 62, personal computer 69, or other computing device connectable over the network 61, when the monitor recorder 14 is appropriately equipped for interfacing with such devices. In one embodiment, network 61 can be a telecommunications network, such as the Internet or a cellular network, and the wireless transceiver can have at least some cellular phone capabilities, such as by being able to connect to the telecommunications networks. For example, if implemented using the standard such as Bluetooth® 4.2 standard or a Wi-Fi standard, the transceiver can connect to the Internet. Similarly, if implemented using a cellular standard and including a cellular chipset, the transceiver can connect to a cellular network as further described below. Once connected, the monitor recorder 14 can interface with the above-described devices via connecting to the telecommunications network. Still other types of remote interfacing of the monitor recorder 14 are possible.

Figure 7:
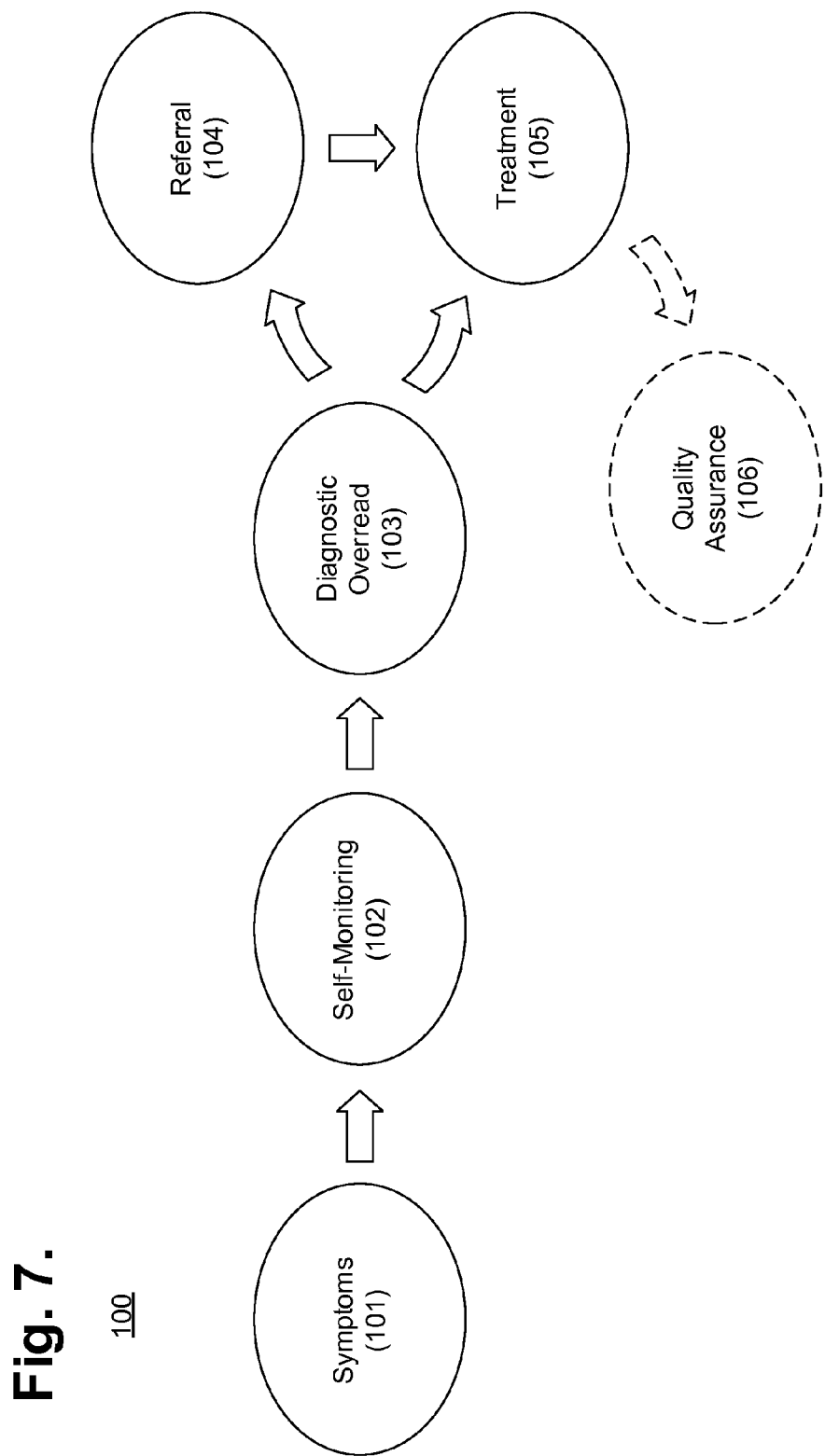
FIG. 7 is a process flow diagram showing a method addressing medical conditions through a wearable health monitor with the aid of a digital computer in accordance with one embodiment.

The wearable monitor 12 records a patient's cardiac activity, with an emphasis on sensing atrial activity and, to a lesser extent, ventricular activity, over an extended period of monitoring. The wearable monitor 12 could include additional sensors to monitor and record other types of physiology, including blood pressure, respiratory rate, temperature, and blood glucose, either in addition to or in lieu of heart rate. FIG. 7 is a process flow diagram showing a method 100 addressing medical conditions through a wearable health monitor 12 with the aid of a digital computer 62 in accordance with one embodiment. The method 100 can be implemented with the aid of software, firmware or hardware and execution of the method 100 can be performed in salient part on a download station 65, which could be a programmer or other device, or a digital computer, including a server 62 or personal computer 76, as a series of process or method modules or steps. For convenience, the method 100 will be described in the context of being performed by a digital computer. Execution of the method 100 by other types of computing devices would be analogous mutatis mutandis.

At the outset, a patient suffering symptoms indicative of a non-urgent physical ailment or health condition (step 101) will obtain a wearable monitor 12, or similar device, and initiate self-monitoring (step 102). The wearable monitor 12 will record the patient's ECG and physiology data over a monitoring period and the data will be recorded into an onboard memory. Upon completion of the monitoring period, the ECG and physiology data will be downloaded into a digital computer with, for instance, the assistance of a download station 65 or similar device, or via wireless connection, if the wearable monitor 12 is so equipped.

The ECG and physiology data 79 retrieved from the wearable monitor 12 is evaluated to identify situations in which the patient requires specific actionable health care. The digital computer generates a diagnostic overread (step 103) of the ECG and physiology data 79 by comparing the data to a set of diagnostic criteria 80. The ECG and physiology data 79 may be structured along a temporal spectrum that reflects changes in physiology over time, or could be structured on a per event basis where a change in physiology alone suffices to raise a concern. A diagnostic criteria 80 can be defined generally for classes of health conditions, such as cardiac disorder, respiratory distress, hypoglycemia, and hypoxia, or for specific medical conditions, for instance, light headedness that consists of near syncope, atrial fibrillation that consists of episodes longer than 1 minute, ectopy that consists, on average, of over 3 PVCs per minute, palpitations that consist of rapid fluttering over the left side of the chest, supraventricular tachycardia that consists of rates greater than 180 bpm, ventricular tachycardia that consists of more than 3 ventricular beats in a row, bradycardia that consists of pauses greater than 3 seconds, or heart blockage that consists of unconducted normal sinus impulses. Other diagnostic criteria are possible.

Diagnostic findings 81 are made for each of the diagnostic criteria 80. The diagnostic findings 81 are rated by the digital computer by degree of severity and compared to a threshold level of tolerance for each finding. The diagnostic findings 81 may be tailored to a specific client, disease or medical condition group, or applied to a general patient population. If any of the diagnostic findings 81 rate severely enough to warrant medical attention, a referral 83 is automatically generated on behalf of the patient to a pre-identified care provider (step 104) primarily when the patient's medical condition is novel and has not previously been noted in the patient's medical history, although a referral may still be appropriate in some situations where the medical condition has already presented. When the patient's medical condition is pre-existing, the patient may be told to seek immediate medical treatment with a pre-identified medical facility (step 105), thereby bypassing the sequential and laggard referral route, although a referral and immediate medical treatment could both be triggered regardless of medical condition, should the patient so desire, regardless of monitoring outcome. In this instance, where the monitor shows only normal activity or unactionable activity, the patient will likely be referred to a general practitioner.

The foregoing solution to addressing a patient's medical conditions can happen without having to preemptively involve health insurance. Moreover, the wearable monitor 12 works particularly well with medical conditions that defy in-clinic testing. In addition, a database of pre-identified care providers ordered by medical specialty or other selection criteria can be paired with the diagnostic criteria to ensure that a patient gains access to the appropriate type of medical care required based on the diagnostic findings made for his medical condition. In a further embodiment, quality assurance can be performed (step 106) following the dispatch of a referral to rate the health care received by the patient using metrics such as quality, efficiency, and expediency. Other quality assurance metrics are possible. Still other operations and steps are possible.

While the invention has been particularly shown and described as referenced to the embodiments thereof, those skilled in the art will understand that the foregoing and other changes in form and detail may be made therein without departing from the spirit and scope.

What is claimed is:

1. A health monitoring apparatus for addressing medical conditions with the aid of a digital computer, comprising:
   a wearable health monitor comprising:
      a disposable extended wear electrode patch comprising:
         a flexible backing comprising stretchable material defined as an elongated strip with a narrow longitudinal midsection, each end of the flexible backing comprising an adhesive contact surface adapted to serve as a crimp relief;
         a plurality of electrocardiographic electrodes comprised on the contact surface of each end of the flexible backing and provided to sense a patient's physiology over a monitoring period, each electrocardiographic electrode conductively exposed for dermal adhesion and adapted to be positioned axially along the midline of the sternum for capturing action potential propagation;
         a non-conductive receptacle affixed to a non-contacting surface of the flexible backing and comprising an electro mechanical docking interface; and
         a pair of flexible circuit traces affixed at each end of the flexible backing with each circuit trace connecting one of the electrocardiographic electrodes to the docking interface, at least one of the circuit traces adapted to extend along the narrow longitudinal midsection to serve as a strain relief; and
      a monitor recorder capable of recording the physiology throughout the monitoring period, comprising:
         a sealed housing adapted to be removably secured into the non-conductive receptacle; and
         electronic circuitry comprised within the sealed housing and comprising an external interface configured to be removably connected to the electrocardiographic electrodes via the docking interface comprising:

an externally-powered microcontroller operable to execute under micro programmable control through firmware that is stored in a program memory unit of the microcontroller;

an electrocardiographic front end circuit electrically interfaced to a microcontroller and operable to sense electrocardiographic signals through the electrocardiographic electrodes; and an externally-powered flash memory electrically interfaced with the microcontroller and operable to store samples of the electrocardiographic signals collected during the execution of the monitoring sequence;

a download station comprising an interface over which the physiology can be downloaded from the onboard memory of the wearable heath monitor upon completion of the monitoring period; and a computer adapted to be interfaced to the download station, comprising:

a database, comprising:

the physiology as retrieved from the download station; and a medical diagnostic criteria;

a processor and a memory configured to store code executable by the processor and comprising:

a comparison module configured to compare the physiology to the medical diagnostic criteria and to generate a diagnostic overread that comprises one or more diagnostic findings; and a referral module configured to determine the severity of any medical condition indicated by the diagnostic findings and to refer the patient to one or more pre-identified care providers via the computer for facilitated diagnosis as conditioned upon the severity of each such medical condition that exceeds a threshold tolerance level.

2. A health monitoring apparatus according to claim 1, the monitor recorder further comprising:

the microcontroller operable to detect the electrocardiographic electrodes being adhered to the sternum based on the sensed electrocardiographic signals and to start an execution of a monitoring sequence stored as part of the firmware based on the detected adherence.

3. A health monitoring apparatus according to claim 2, further comprising:

a wireless transceiver electrically interfaced with the microcontroller and operable to wirelessly interface with one or more external wireless-enabled devices.

4. A health monitoring apparatus according to claim 3, wherein one of the wireless-enabled devices is a mobile phone and the wireless transceiver interfaces with the mobile phone via a telecommunications network.

5. A health monitoring apparatus according to claim 4, wherein the wireless-enabled device communicates the received samples to the computer to evaluate to evaluate the samples of the electrocardiographic signals and to refer the patient to the one or more pre-identified care providers.

6. A health monitoring apparatus according to claim 1, the referral module further comprising at least one of:

a notification module configured to notify a general practice physician upon a diagnostic finding comprising normal physiological data despite patient complaints of light headedness or syncope;

a notification module configured to notify a cardiologist upon a diagnostic finding comprising atrial fibrillation of over 1 minute duration, ectopy comprising more than 3 PVCs per minute, palpitations comprising fluttering of the chest, and supraventricular tachycardia comprising heart rates over 180 bpm; and a notification module configured to notify an electrophysiologist upon a diagnostic finding comprising ventricular tachycardia comprising 3 or more consecutive abnormal ventricular beats, bradycardia comprising pauses greater than 3 seconds, and heart blockage comprising the non-conduction of any normal sinus beat.

7. A health monitoring apparatus according to claim 1, the database further comprising the pre-identified care providers ordered by medical specialty and paired with one or more of the diagnostic criteria.

8. A health monitoring apparatus according to claim 1, the database further comprising a medical history for the patient, wherein the medical history is incorporated into the comparison against the diagnostic criteria.

9. A health monitoring apparatus according to claim 8, the referral module further comprising:

a notification module configured to generate a referral to one such care provider if the diagnostic findings comprises a medical condition not found in the patient's medical history; and a notification module configured to engage proactive health care management if the diagnostic findings comprises a medical condition found in the patient's medical history.

10. A health monitoring apparatus according to claim 1, the database further comprising at least one of:

the diagnostic criteria along a temporal spectrum comprising changes in the physiology for at least one of the diagnostic findings over time; and the diagnostic criteria on a per event basis comprising a change in the physiology for at least one of the diagnostic findings.

* * * * *